(12) United States Patent
Torihashi et al.

(10) Patent No.: US 8,470,595 B2
(45) Date of Patent: Jun. 25, 2013

(54) MESENCHYMAL STEM CELL AND METHOD FOR PRODUCTION THEREOF

(75) Inventors: Shigeko Torihashi, Nagoya (JP); Nana Ninagawa, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 0 days.

(21) Appl. No.: 12/988,381

(22) PCT Filed: Apr. 17, 2009

(86) PCT No.: PCT/JP2009/057766
§ 371 (c)(1),
(2), (4) Date: Dec. 28, 2010

(87) PCT Pub. No.: WO2009/128533
PCT Pub. Date: Oct. 22, 2009

(65) Prior Publication Data
US 2011/0111499 A1 May 12, 2011

(30) Foreign Application Priority Data
Apr. 18, 2008 (JP) .................................. 2008-109002

(51) Int. Cl.
*C12N 5/10* (2006.01)
*C12N 5/06* (2006.01)
(52) U.S. Cl.
USPC ........................ 435/325; 435/377; 424/93.7
(58) Field of Classification Search
None
See application file for complete search history.

(56) References Cited

U.S. PATENT DOCUMENTS

| | | |
|---|---|---|
| 2005/0221327 A1 | 10/2005 | Lundgren-Akerlund |
| 2007/0053885 A1 | 3/2007 | Nishikawa et al. |
| 2007/0128727 A1 | 6/2007 | Kraemer et al. |
| 2008/0219957 A1* | 9/2008 | Lim et al. .................... 424/93.7 |
| 2008/0241171 A1 | 10/2008 | Gentry et al. |

OTHER PUBLICATIONS

Dani et al., Differentiation of embryonic stem cells into adipocytes in vitro, Journal of Cell Science 110, 1279-1285 (1997).*
Barberi et al., Derivation of engraftable skeletal myoblasts from human embryonic stem cells, Nature Medicine, vol. 13, No. 5, May 2007.*
Lian et al., Derivation of Clinically Compliant MSCs from CD105+, CD24− Differentiated Human ESCs, Stemcells 2007;25:425-436.*
Thomas et al., Embryonic Stem Cell Lines Derived from Human Blastocysts, Science 282, 1145 (1998).*

(Continued)

*Primary Examiner* — James Ketter
*Assistant Examiner* — Reza Ghafoorian
(74) *Attorney, Agent, or Firm* — Turocy & Watson, LLP (57) ABSTRACT

The present invention provides a method for producing a mesenchymal stem cell having an ability to differentiate into a myoblast by culturing a pluripotent stem cell derived from a human or animal, including: i) preparing the pluripotent stem cell that has been cryopreserved, ii) sub-culturing the prepared pluripotent stem cell in an undifferentiated state for a prescribed number of times, iii) culturing the subcultured pluripotent stem cell under conditions that enable induction of differentiation into an adipocyte in vitro, and iv) separating and collecting a CD105-positive cell during the culturing process.

4 Claims, 8 Drawing Sheets

OTHER PUBLICATIONS

Lim et al., A Shortened Life Span of EKLF−/− Adult Erythrocytes, Due to a Deficiency of β-Globin Chains, Is Ameliorated by Human γ-Globin Chains, Blood 1997 90: 1291-1299.*

BD Biosciences, "BD Biosciences Human CD Marker Char," published by Becton, Dickinson and Company at http://www.bdbiosciences.com/documents/Human_CD_Chart.pdf, copyright 2010, downloaded May 29, 2012.*

Wdziekonski et al., Differentiation of Mouse Embryonic Stem Cells and of Human Adult Stem Cells into Adipocytes, Current Protocols in Cell Biology (2007) 23.4.1-23.4.14.*

Barberi et al., Derivation of Multipotent Mesenchymal Precursors from Human Embryonic Stem Cells, PLoS Med 2(6): e161, (2005).*

Montoya et al., Culture Systems for Pluripotent Stem Cells, Journal of Bioscience and Bioengineering, vol. 100, No. 1, 12-27 (2005).*

Stojkovic et al., Derivation, growth and applications of human embryonic stem cells, Reproduction (2004) 128, pp. 259-267.*

International Search Report for PCT/JP2009/057766 Mailed May 26, 2009.

* cited by examiner

PLURIPOTENT STEM CELL PASSAGE NUMBER

MESENCHYMAL STEM CELL AND METHOD FOR PRODUCTION THEREOF

TECHNICAL FIELD

The present invention relates to a mesenchymal stem cell obtained during the course of inducing differentiation from a pluripotent stem cell into an adipocyte, and to a production method thereof. More particularly, the present invention relates to a CD105-positive mesenchymal stem cell capable of differentiating into a myoblast at a high rate, and to a production method thereof.

The present international application claims priority on the basis of Japanese Patent Application No. 2008-109002 filed on Apr. 18, 2008, the entire contents of which are incorporated herein by reference.

BACKGROUND ART

Efforts are proceeding in the field of regenerative medicine for regenerating cells, tissues or organs and recovering their functions that were lost due to illness or accident and the like by using artificially cultured cells and tissues. In particular, a search is being made for safe and effective cells that are compatible with transplantation for use in treatment of lifestyle diseases such as arteriosclerosis, myocardial infarction, liver cirrhosis or diabetes as well as refractory diseases for which there are no effective therapeutic drugs such as Parkinson's disease or muscular dystrophy.

Mesenchymal stem cells (MSC) are cells that have the ability to differentiate into different types of various mesenchymal cells such as adipocytes, osteocytes, chondrocytes, fibroblasts or myoblasts, and since they permit autologous transplantation, are one of the cells that are expected to be applied to regenerative medicine.

Although mesenchymal cells are known to exist in human bone marrow as mesenchymal stem cells derived from bone marrow, since the number of such cells that can be separated and purified from bone marrow is extremely low, methods are attracting attention that enable mesenchymal stem cells to be obtained in large quantities from other body tissues, and particularly adipose tissue (referred to as adipose-derived stem cells (ADSCs)). ADSCs separated from adipose tissue have been reported to have the ability to multidifferentiate into adipocytes and osteocytes as well as immunotolerance (Non-Patent Documents 1 to 4).

Non-Patent Document 1: Zuk, P. A. et al., Mol. Biol. Cell, 13: 4279-4295, 2002
Non-Patent Document 2: Zuk, P. A. et al., Tissue Eng., 7: 211-228, 2001
Non-Patent Document 3: Rodriguez, A. M. et al., J. Exp. Med., 201: 1397-1405, 2005
Non-Patent Document 4: Qu-Petersen, et al., J. Cell. Biol., 157: 851-864, 2002

However, various types of cells such as neurocytes, vascular cells and adipocytes are also present in addition to ADSCs in human adipose tissue, and it is difficult to efficiently separate ADSCs from this tissue.

In addition, although ADSCs separated from adipose tissue have the ability to multidifferentiate, it is known to be extremely difficult to induce differentiation of ADSCs into myoblasts as compared with inducing their differentiation into adipocytes or osteocytes. Myoblasts fuse together to form tubular myotubes, and as they continue to differentiate, they ultimately become precursor cells that form skeletal muscle, and are useful cells in regenerative medicine.

Thus, an object of the present invention is to separate and collect mesenchymal stem cells that differentiate into myoblasts as efficiently as possible and in large quantities as an alternative to ADSCs.

DISCLOSURE OF THE INVENTION

With the foregoing in view, a main object of the present invention is to provide a method for efficiently and in large quantity producing a mesenchymal stem cell capable of differentiating into a myoblast during the course of inducing differentiation from a pluripotent stem cell into an adipocyte. In addition, another object is to provide a cell culture obtained according to the above-mentioned production method that contains a high percentage of mesenchymal stem cells capable of differentiating into myoblasts. In addition, another object is to provide a method for producing cells that have efficiently differentiated from a pluripotent stem cell into a target form (such as adipocytes, osteocytes, chondrocytes or myoblasts) by using the above-mentioned method and/or cell culture.

In order to solve the above-mentioned problems, the cell culture provided by the present invention is a cell culture containing CD105-positive mesenchymal stem cells that have been differentiated from pluripotent stem cells derived from a human or animal, wherein at least a portion of the cells contained in the culture are cells that have an ability to differentiate into myoblasts by culturing the pluripotent stem cells under conditions that enable induction of differentiation into adipocytes.

Furthermore, in the present description, a "pluripotent stem cell" refers to an undifferentiated cell having pluripotency and self-replicating ability that is able to differentiate into various tissues that compose the adult body, and an embryonal carcinoma cell (EC cell), embryonic stem cell (ES cell), embryonic germ cell (EG cell) or induced pluripotent stem cell (iPS cell) are typical examples of pluripotent stem cells as referred to here. In addition, in the present description, a pluripotent stem cell refers to a pluripotent stem cell derived from a human or animal (and typically a mammal).

In addition, in the present description, a "mesenchymal stem cell" refers to an undifferentiated cell that has a self-replicating ability and the ability to differentiate into various mesenchymal cells such as an adipocyte, chondrocyte, osteocyte, myoblast, fibroblast, stromal cell or tenocyte. Although mesenchymal stem cells are typically present in bone marrow in the body, there are various tissue-derived mesenchymal stem cells that have been separated from other tissues such as adipose tissue, umbilical cord blood or dental pulp.

In addition, in the present description, "CD105" refers to a receptor of TGF-β, which is a growth and differentiation factor, that is a protein expressed on the cell surface of ADSCs, in precursor cells of blood vessels and blood cells, and in bone marrow-derived stem cells.

When the inventors of the present invention produced a cell culture containing CD105-positive mesenchymal stem cells during the course of inducing differentiation from pluripotent stem cells derived from a human or animal into adipocytes by utilizing the self-replication ability and pluripotency of pluripotent stem cells that enables them to differentiate into various mesenchymal cells, the mesenchymal stem cells are found to include cells that have the ability to differentiate into myoblasts, thereby leading to completion of the present invention. Thus, when the mesenchymal stem cells are separated and collected, and sub-cultured under respective conditions enabling induction of differentiation into a target cell (such as an adipocyte, osteocyte, chondrocyte or myoblast, and typically a myoblast), a cell is obtained that has been differentiated into a target form (such as an adipocyte, osteocyte, chondrocyte or myoblast, and typically a myoblast). For example, a fusiform myoblast is obtained by culturing the above-mentioned CD105-positive cell culture under conditions that enable induction of differentiation into myoblasts.

Myoblasts are precursors of skeletal muscle that have sophisticated functions, and it is more difficult to induce their differentiation from mesenchymal stem cells in comparison with inducing differentiation into adipocytes or osteocytes. However, according to the present invention disclosed herein, a cell culture can be easily and in large quantity obtained that contains a high percentage of cells having the ability to differentiate into myoblasts during the course of inducing differentiation from a pluripotent stem cell derived from a human or animal into an adipocyte.

Namely, the present invention provides a cell having an ability to differentiate into a myoblast for use as a transplanted cell. According to the present invention, a cell culture can be preferably provided for use in regenerative medicine that is able to contribute to improvement of function and formation of tissue at sites having a wide-ranging muscle deficit or sites having impaired function.

In a preferable aspect of the cell culture disclosed herein, the pluripotent stem cell derived from a human or animal is an ES cell.

The ES cell is useful as the pluripotent stem cell relating to the present invention since it has a high proliferation ability and pluripotency enabling it to differentiate into various cells, thereby making it preferable.

In addition, in another preferable aspect of the cell culture disclosed herein, the pluripotent cell derived from a human or animal is an iPS cell. An iPS cell has properties similar to an ES cell, and in consideration of not involving ethical issues as a result of being produced from somatic cells, is a particularly preferable pluripotent stem cell in terms of achieving the object of the present invention.

In addition, in another preferable aspect of the cell culture disclosed herein, the cell culture contains myoblasts that have been differentiated from the mesenchymal stem cells. According to the cell culture of this aspect, a myoblast can be provided that has been differentiated from the stem cells.

In addition, in another preferable aspect of the cell culture disclosed herein, at least 50% or more (and particularly preferably 80% or more) of the cells are the mesenchymal stem cells. According to the cell culture of this aspect, myoblasts can be provided that have been differentiated from the stem cells at a high rate.

Moreover, in another aspect that realizes the above-mentioned object, the present invention provides a method for producing a mesenchymal stem cell that has an ability to differentiate into a myoblast by culturing a pluripotent stem cell derived from a human or animal.

The method disclosed herein comprises: i) preparing the pluripotent stem cell that has been cryopreserved, ii) sub-culturing the prepared pluripotent stem cell in an undifferentiated state for a prescribed number of times, iii) culturing the subcultured pluripotent stem cell under conditions that enable induction of differentiation into an adipocyte in vitro, and iv) separating and collecting a CD105-positive cell during the culturing process.

In the production method relating to the present invention, only a mesenchymal stem cell that has expressed CD105 is separated and collected from cells that appear prior to formation of an adipocyte during the course of inducing differentiation from pluripotent stem cell derived from a human or animal into an adipocyte. Thus, the method does not involve complex treatment in the manner of extracting only ADSCs from adipose tissue in which various types of cells such as neurocytes, vascular cells or adipocytes are present as is the case with ADSCs. Namely, a mesenchymal stem cell can be produced efficiently and in large quantities during the course of culturing that induces differentiation of pluripotent stem cells into adipocytes.

In the production method of the present invention, the pluripotent stem cell that has been cryopreserved is allowed to self-replicate prior to carrying out induction of differentiation into an adipocyte, or in other words, is sub-cultured for a prescribed number of times in an undifferentiated state. As a result, the efficiency at which a mesenchymal stem cell is induced to differentiate into an adipocyte can be improved.

In the case of an ES cell, for example, after repeatedly sub-culturing an ES cell that has been cryopreserved (without limiting to an ES cell that has been newly established from an inner cell mass within an embryo or a previously established ES cell) in the presence of a leukemia inhibitory factor (LIF), induction of differentiation into an adipocyte is carried out. As a result of sub-culturing an undifferentiated state in this manner, the number of cryopreserved pluripotent stem cells can be increased to a number of cells suitable for inducing differentiation.

In addition, in a preferable aspect of the method disclosed herein, the sub-culturing is carried out for 8 to 12 times (and particularly preferably 9 to 11 times) in an undifferentiated state. As a result of carrying out sub-culturing under conditions that induce differentiation into an adipocyte using a pluripotent stem cell that has been sub-cultured 8 to 12 times, the ability of the resulting CD105-positive mesenchymal stem cell to differentiate into a myoblast can be remarkably improved.

Namely, according to the production method of the present aspect, by carrying out sub-culturing of a pluripotent stem cell 8 to 12 times (and particularly preferably 9 to 11 times) after thawing, a mesenchymal stem cell having an ability that enables it to be induced to differentiate into a myoblast can be obtained in a large quantity. As a result, in the method of this aspect, a mesenchymal stem cell can be provided that is able to fulfill the role of an extremely useful therapeutic material in the field of regenerative medicine.

In another preferable aspect of the method disclosed herein, culturing is carried out under conditions that enable induction of differentiation into an adipocyte in vitro. An example of a typical condition for enabling induction of differentiation includes suspension-culturing in a culture broth supplemented with retinoic acid, followed by culturing in a culture broth supplemented with insulin and triiodothyronine (T3). For example, suspension culturing in a culture broth supplemented with retinoic acid is preferably carried out for several days (for example, 2 to 3 days and particularly preferably 2 days). When induction of differentiation is carried out in vitro using this culture broth, differentiation into a pluripotent stem cell is promoted, and a mesenchymal stem cell can be expressed at a high rate during the course of culturing.

In addition, in another preferable aspect of the method disclosed herein, culturing under conditions that enable induction of differentiation of the pluripotent stem cell following the sub-culturing described above is carried out for a time period not exceeding 21 days. Since the probability of the pluripotent stem cell differentiating into an adipocyte increases if culturing is carried out for a time period of 21 days or more, the efficiency of separation and collection of a mesenchymal stem cell that is expressed prior to differentiation into an adipocyte decreases, thereby making this undesirable. Thus, treatment for separating a CD105-positive cell to be subsequently described is preferably carried out by culturing for a time period that does not exceed 21 days from the start of culturing following sub-culturing (and typically, 7 to 21 days, preferably 7 to 14 days and particularly preferably 12 to 14 days).

Moreover, in another preferable aspect of the method disclosed herein, various cell sorting methods are used as means for separating a CD105-positive cell. A particularly preferable aspect thereof is a magnetic cell sorting method (MACS® method). For example, an example of this method includes preparing a labeled molecule in which pre-magnetized beads are loaded onto anti-CD105 antibody, binding the labeled molecule to a cell surface by an antigen-antibody reaction with a cell expressing CD105, and separating only a CD105-positive cell to which the labeled molecule is bound with a magnet. In this manner, according to the method of the present aspect, a CD105-positive cell expressing CD105 on the surface thereof (namely, a mesenchymal stem cell) can be efficiently obtained (separated and collected) in large quantity without having to carry out a complex, bothersome procedure.

In addition, in another aspect that realizes the above-mentioned object, the present invention provides a method for producing a cell that has differentiated into a target form (such as an adipocyte, osteocyte, chondrocyte or myoblast, and typically a myoblast) by culturing a pluripotent stem cell derived from a human or animal.

This method comprises: i) preparing the pluripotent stem cell that has been cryopreserved, ii) sub-culturing the prepared pluripotent stem cell in an undifferentiated state for a prescribed number of times, iii) culturing the subcultured pluripotent stem cell under conditions that enable induction of differentiation into an adipocyte in vitro, iv) separating and collecting a CD105-positive mesenchymal stem cell during the culturing process, and v) culturing the separated and collected CD105-positive cell under respective conditions which enable induction of differentiation into a target cell in vitro (such as an adipocyte, osteocyte, chondrocyte or myoblast, and typically a myoblast).

Preferably, an ES cell is used for the pluripotent stem cell.

In addition, the pluripotent stem cell is preferably sub-cultured 8 to 12 times (and particularly preferably 9 to 11 times).

BEST MODE FOR CARRYING OUT THE INVENTION

The following provides an explanation of a preferred embodiment of the present invention. Furthermore, those matters other than specifically mentioned in the present description (such as methods for producing mesenchymal stem cells) that are required for carrying out the present invention (such as methods for sub-culturing pluripotent stem cells, conditions for inducing differentiation into adipocytes, conditions for inducing differentiation into osteocytes, conditions for inducing differentiation into chondrocytes, or conditions for inducing differentiation into myoblasts) can be understood to be design matters of a person with ordinary skill in the art based on the prior art in fields such as medicine, pharmacology, biochemistry, organic chemistry, protein engineering, molecular biology, veterinary medicine or hygiene. The present invention can be carried out based on the technical contents disclosed in the present specification and common general technical knowledge in the relevant field.

As was previously described, the method disclosed herein is a method for producing efficiently and in large quantity a mesenchymal stem cell capable of differentiating into a myoblast during the course of inducing to differentiate from a pluripotent stem cell into an adipocyte, and includes the steps indicated below.

The method for producing a mesenchymal stem cell relating to the present invention includes: i) preparing the pluripotent stem cell that has been cryopreserved, ii) sub-culturing the prepared pluripotent stem cell for a prescribed number of times in an undifferentiated state, iii) culturing the sub-cultured pluripotent stem cell under conditions that enable induction of differentiation into an adipocyte in vitro, and iv) separating and collecting a CD105-positive mesenchymal stem cell during the course of the culturing.

Moreover, by v) further culturing the separated and collected CD105-positive cell under respective conditions enabling the cell to be induced to differentiate into a target cell (such as an adipocyte, osteocyte, chondrocyte or myoblast, and typically a myoblast) in vitro, a cell can be produced that has differentiated to a target form (such as an adipocyte, osteocyte, chondrocyte or myoblast, and typically a myoblast).

The following provides a detailed explanation of the method for producing a mesenchymal stem cell relating to the present invention, and a method for producing a myoblast or other target cell by inducing the mesenchymal stem cell to differentiate.

There are no particular limitations on the pluripotent stem cell used provided it realizes the object of the present invention. Although examples of the pluripotent stem cell include cells such as EC cells, ES cells, EG cells and iPS cells that have the ability to self-replicate and pluripotency that enables the cell to differentiate into various tissues that compose an adult body, typical examples to which the technology disclosed herein is preferably applied include human or animal-derived ES cells, or iPS cells.

Examples of ES cells include those that have been established so as to be able to cultured in vitro by extracting pluripotent stem cells from an inner cell mass (embryo within 14 days after conception in a mammal). Culturing of ES cells can be carried out by, for example, proliferating while maintaining in an undifferentiated state in the presence of LIF. On the other hand, cell differentiation can be induced in the same manner as early embryos in the absence of LIF. ES cells used in the present invention are not limited to ES cells that have been newly established from an inner cell mass within an embryo or previously established ES cells.

In addition, the origin of the ES cells is preferably either human or animal. ES cells derived from a mammal such as a human, monkey, mouse, rat, hamster, rabbit, dog, cat, sheep or pig can be used preferably. ES cell lines registered in a cell bank or commercially available ES cell lines can be used as animal-derived ES cells. However, human-derived ES cells are used preferably when treating a human. Furthermore, human-derived ES cells are required to be handled reliably and carefully so as not to infringe on human rights in consideration of the fact that embryos constitute the origin of life and that human-derived ES cells have the potential to differentiate into all cells.

An example of other pluripotent stem cells preferable for carrying out the present invention is iPS cells. iPS cells are cells that have been artificially constructed into cells having pluripotency from somatic cells (and typically, fibroblasts) derived from any body tissue (such as skin tissue) without using a fertilized egg in the manner of ES cells. Namely, since these cells are produced from cells from patients themselves, they are expected to be applied to regenerative medicine as a form of treatment conducted for the purpose of improving function or regenerating tissue at sites of tissue deficit or sites of impaired function without causing a rejection reaction.

In addition, pluripotent stem cells such as the above-mentioned ES cells or iPS cells that have been cryopreserved can be preferably used for the pluripotent stem cell relating to the present invention. The prepared pluripotent stem cell is preferably sub-cultured in an undifferentiated state prior to inducing to differentiate into an adipocyte. As a result of sub-culturing for a prescribed number of times, the cryopreserved pluripotent stem cell can be proliferated to a number of cells suitable for inducing differentiation. In addition, the efficiency of inducing to differentiate into a desired cell type can be improved.

Although sub-culturing is typically and commonly carried out for 5 to 17 times, in the present invention, sub-culturing is preferably carried out 8 to 12 times (and particularly preferably 9 to 11 times). Culturing is carried out under conditions that induce differentiation into an adipocyte using a cryopreserved pluripotent stem cell that has been sub-cultured 8 to 12 times (and particularly preferably 9 to 11 times) after thawing. As a result, the differentiation ability (probability) of the resulting CD105-positive mesenchymal stem cell into a myoblast can be remarkably improved.

Any conventionally used induction method may be used to induce differentiation into an adipocyte in vitro, and although there are no particular limitations thereon, differentiation is typically induced by suspension-culturing in a culture broth supplemented with retinoic acid for several days (for example, 2 to 3 days and particularly preferably 2 days) followed by culturing in a culture broth supplemented with insulin and triiodothyronine (T3). The culture broth composition described in the following examples is a preferable example thereof.

In addition, culturing conditions conventionally used for culturing this type of cell can be used as long as the object of the present invention is realized, and there are no particular limitations thereon with respect to the type of medium, contents of constituents, concentration of constituents or culturing temperature and the like.

In addition, the duration of culturing preferably is a time period that typically does not exceed 21 days. If a pluripotent stem cell that has been induced to differentiate into an adipocyte is continued to be cultured for a long period of time of 21 days or more, those cells that have differentiated into adipocytes account for the majority of the cells, thereby making this undesirable. Thus, CD105-positive cells are preferably separated and collected using a separation method to be described later within a time period that does not exceed 21 days from the start of culturing (typically 7 to 21 days, preferably 7 to 14 days and particularly preferably 12 to 14 days).

Although a various conventionally known methods can be used as means for separating and collecting expressed CD105-positive cells, various cell sorting methods can be used as preferable means thereof. Examples of such methods include separation methods using a cell sorter or flow cytometer using fluorescence activated cell sorting (FACS), and magnetic cell sorting (MACS®). Since a method for inducing differentiation of a pluripotent stem cell is used in the present invention, differing from methods involving isolation from body tissues, the expressed amount of mesenchymal stem cells in the cell culture is comparatively large. Thus, MACS® can be used preferably since it allows mesenchymal stem cells (namely, CD105-positive cells) expressed in large quantities to be separated easily and efficiently.

More specifically, CD105-positive cells can be selectively separated and collected by MACS® by using cells in which magnetic beads are loaded onto anti-CD105 antibody that specifically binds to CD105 (or secondary antibody that specifically binds to that antibody).

In addition, in order to increase the purification rate of cells that have been separated and collected by MACS®, the cells that have been separated by MACS can be further purified using an FACS® method such as that which uses a cell sorter or flow cytometer.

In addition, the cell culture obtained according to the production method disclosed herein is a cell culture that contains CD105-positive mesenchymal stem cells (preferably at a ratio of 50% or more the total number of cells) expressed by culturing under conditions that induce differentiation of human or animal-derived pluripotent stem cells into adipocytes, and may also contain other cells. For example, in a preferable aspect thereof, at least a portion of the cells in the cell culture are cells that have an ability to differentiate into myoblasts. In this aspect as well, various cells other than the above-mentioned cells may also be contained in the cell culture provided they do not inhibit induction of differentiation into myoblasts.

The CD105-positive mesenchymal stem cells contained in the cell culture can be confirmed by, for example, CD105 immunofluorescent staining. A cell culture broth in which at least 50% or more (and preferably 80% or more) of all cells (viable cells) in the cell culture are observed to be CD105-positive mesenchymal stem cells is a preferable aspect of a cell culture broth relating to the present invention, and by culturing under respective conditions that enable the mesenchymal stem cells to be induced to differentiate into a target cell (such as an adipocyte, osteocyte, chondrocyte or myoblast, and typically a myoblast), cells that have differentiated into a target form (such as an adipocyte, osteocyte, chondrocyte or myoblast, and typically a myoblast) can be provided at a high rate.

The presence of cells in the cell culture that are able to be induced to differentiate into a target cell can be confirmed by separating and collecting CD105-positive cells in the manner described above followed by using various biochemical approaches or morphological observation during the course of continuing to culture the separated cells under respective culturing conditions.

For example, the type of differentiated cell can be identified by various confirmation methods such as microscopic observation, various cell staining methods, northern blotting using hybridization or RT-PCR. In particular, since myoblasts having a fusiform cell exterior and have a characteristic morphology, they can be easily identified by observing cell morphology. Alternatively, the presence of myoblasts can be confirmed by immunofluorescent staining using anti-M-cadherin antibody or immunofluorescent staining using anti-myosin heavy chain (MHC) antibody.

On the other hand, although adipocytes, osteocytes and chondrocytes are difficult to identify from their morphology, the presence of adipocytes can be confirmed by staining intracellular substances (for example, adipocytes can be stained red with Oil Red O stain). In addition, osteocytes can be identified by staining cells with Alizarin red stain. In addition, the presence of chondrocytes can be confirmed by staining cells with Alcian blue stain.

Although the following examples provide detailed explanations of preferable examples of the method that enables efficient production of mesenchymal stem cells having the ability to differentiate into myoblasts relating to the present invention (or in other words, the method for efficiently producing myoblasts), the following examples are not intended to limit the present invention.

[Sub-culturing of Pluripotent Stem Cells]

Mouse-derived ES cells were used as pluripotent stem cells in the present example.

An ES cell culture broth (ES-DMEM) was prepared by adding 10% fetal bovine serum (FBS: VMS1500, Vitromex), 1% non-essential amino acids (NEAA: 11140-50, GIBCO®), 1% sodium pyruvate (11360-070, GIBCO®), $7\times10^{-6}\%$ 2-mercaptoethanol (M3148, SIGMA®) and 0.5% antibiotic antimycotic (15240-096, GIBCO®) to Dulbecco's modified Eagle's medium (DMEM: D-5796, SIGMA®) containing 4500 mg/l of glucose.

Culture dishes having a diameter of 100 mm (353003, FALCON™) coated with Dulbecco's Phosphate Buffered Saline (PBS: D5652-10XIL, SIGMA®) containing 0.1% gelatin (G-1890, Sigma) were used to culture the ES cells. Culture broth in which $10^3$ units of Leukemia Inhibitory Factor (LIF: ESGRO ESG1107, CHEMICON®) were added to ES-DMEM was used to culture ES cells maintained in an undifferentiated state.

After thawing cryopreserved mouse-derived ES cells, the cells were disseminated in a culture dish followed by culturing by adding culture broth in which LIF was added to ES-DMEM. The undifferentiated ES cells were washed twice with PBS when they had proliferated to about 70% of the culture dish, after which the cells were dissociated from the culture dish by adding 0.25% trypsin/1 mM EDTA (L7K5399, Nakalai) diluted three-fold with PBS. The number of cells was counted after centrifuging for 5 minutes at 1200 rpm, and then disseminated in a fresh culture dish so that the number of cells reached a concentration of about $5\times10^5$ cells/dish. Sub-culturing was carried out under conditions of 37° C. and 5% $CO_2$. Designating this as the first round of sub-culturing, this sub-culturing was then repeated 7 to 18 times. More specifically, undifferentiated pluripotent stem cells of a Sample 1 were sub-cultured 7 to 18 times, those of Sample 2 were sub-cultured 9 to 14 times, those of Sample 3 8 to 15 times, and those of Sample 4 7 or 10 to 12 or 14 times.

[Culturing Under Conditions Enabling Induction of Differentiation into Adipocytes]

The sub-cultured undifferentiated ES cells were cultured under conditions that enable the cells to be induced to differentiate into adipocytes.

First, in order to initiate differentiation, an embryoid body (EB) was produced according to the hanging drop method by dropping 10 µl aliquots of a cell suspension containing cells at a concentration of 100 cells/µl onto the cover of a 100 mm diameter culture dish using ES-DMEM culture broth not containing LIF.

The cells were suspension-cultured for 2 days thereafter in a culture broth in which 0.02% all-trans retinoic acid (a type of retinoic acid in which all of the retinoic acid is in the trans form: R2625, Sigma) was added to ES-DMEM, followed by further suspension-culturing for 2 days in ES-DMEM.

Subsequently, the cells were disseminated into a culture dish coated with gelatin, and cultured in culture broth in which 0.005% insulin (I-1882, Sigma) and 0.007% 3,3,5-triiodo-L-thyronine (triiodothyronine (T3): T5516, Sigma) were added to ES-DMEM. The culture broth was replaced every 2 days.

On day 13 of the culturing, expression of CD105-positive cells was confirmed by CD105 immunofluorescent staining of the cultured cells.

First, after washing the cultured cells twice with PBS, rat anti-mouse CD105 monoclonal antibody (Clone: 209701, R&D) diluted 100-fold with PBS was added to the cultured cells followed by carrying out an antigen-antibody reaction for 15 minutes at 37° C. Following completion of the reaction, the test cells were washed twice with PBS followed by fixing the test cells by immersing in 4% paraformaldehyde for 15 minutes. The fixed test cells were washed with PBS for 10 minutes a total of five times, followed by adding Alexa Fluor™ pigment-labeled goat anti-rat IgG antibody (A-11007, Molecular Probes) serving as secondary diluted 400-fold to the test cells and carrying out an antigen-antibody reaction for 1 hour at room temperature. Following this reaction, the test cells were washed with PBS for 30 minutes a total of two times. The cells obtained in this manner were sealed in a water-soluble sealing agent that prevents fluorescent bleaching (PermaFluor™: 43499, Thermo) and then observed with a fluorescence microscope.

Figure 1:
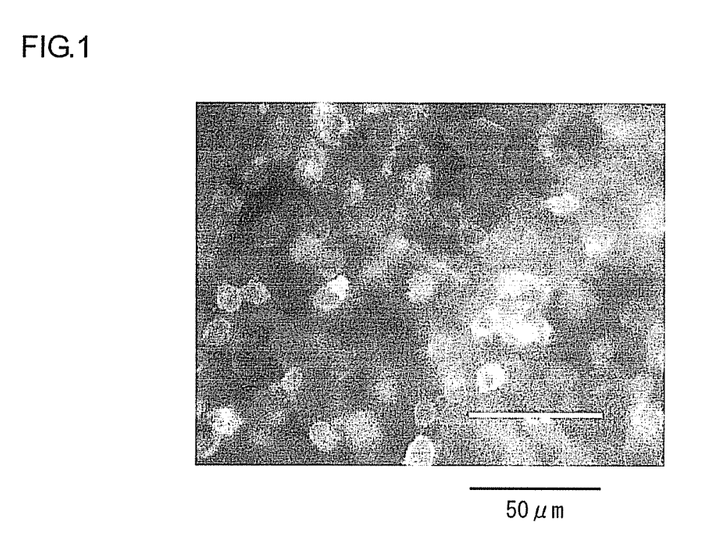
FIG. 1 is a fluorescent micrograph depicting the results of CD105 immunofluorescent staining of pluripotent stem cells on day 13 after culturing under conditions which enable the cells to be induced to differentiate into adipocytes.
Figure 2:
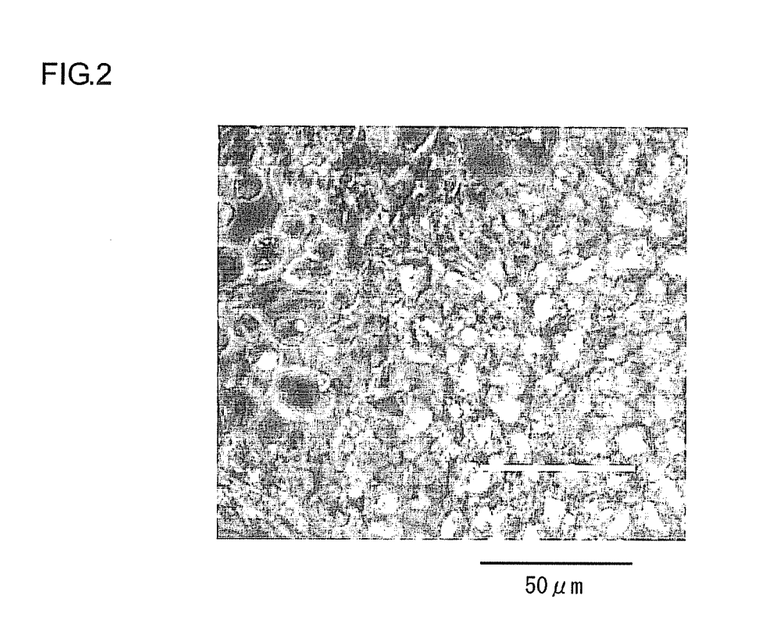
FIG. 2 is a position scanning micrograph depicting the results of CD105 immunofluorescent staining of pluripotent stem cells on day 13 after culturing under conditions which enable the cells to be induced to differentiate into adipocytes.

Micrographs taken at the time of this observation are respectively shown in FIGS. 1 and 2. FIG. 1 is a micrograph taken with a fluorescence microscope. FIG. 2 is a micrograph taken with a position scanning microscope, and both depict the same field.

As is shown in FIGS. 1 and 2, spherical cells were confirmed to be stained red. In addition, the stained cells were confirmed to be present at 50% or more of all cells. Thus, CD105-positive cells were confirmed to be present at a ratio of 50% or more of all cells in the cell culture on day 13 of culturing.

[Separation of CD105-Positive Cells by Magnetic Cell Sorting]

Following the confirmation described above, cells that have been adhered to a culture dish and cultured in an adipogenic induction medium were sorted and collected using a magnetic cell sorting (MACS®) method.

First, after washing the culture dish twice with PBS, 5 mM ethylene diamine tetraacetic acid (EDTA: E-7889, SIGMA®) diluted with PBS was added to the medium followed by allowing to react for 15 minutes at 37° C. to dissociate the cells. Next, the cells were transferred into MACS buffer in which 0.5% bovine serum albumin (BSA: A2934-25G, Sigma) and 2 mM EDTA (E-7889, Sigma) were added to PBS at 4° C., the cell suspension was centrifuged for 5 minutes at 1000 rpm, and the supernatant was aspirated with an aspirator followed by counting the number of cells.

Moreover, rat anti-mouse CD105 monoclonal antibody (Clone: 209701, R&D) diluted 100-fold with PBS was added as primary antibody to the cells followed by carrying out an antigen-antibody reaction for 5 minutes at 4° C. Next, the MACS® buffer was added to the test cells and the cells were washed by centrifuging for 5 minutes at 1000 rpm to remove excess primary antibody. Subsequently, goat anti-rat IgG-bound microbeads (130-048-501, Miltenyl Biotech) diluted 400-fold with PBS were added as secondary antibody to the test cells followed by carrying out an antigen-antibody reaction for 15 minutes at 4° C. Subsequently, the test cells were washed in the same manner as after the reaction with the primary antibody to remove excess secondary antibody.

The cell suspension containing cells labeled with the microbeads obtained in the manner described above was passed through a mini-MACS separation column (Miltenyl Biotech) according to the manual provided by the manufacturer. As a result, the CD105-positive cells were selectively separated. Furthermore, separation by the mini-MACS® separation column was carried out twice in succession to enhance cell purity.

[Yield of CD105-Positive Cells]

Figure 3:
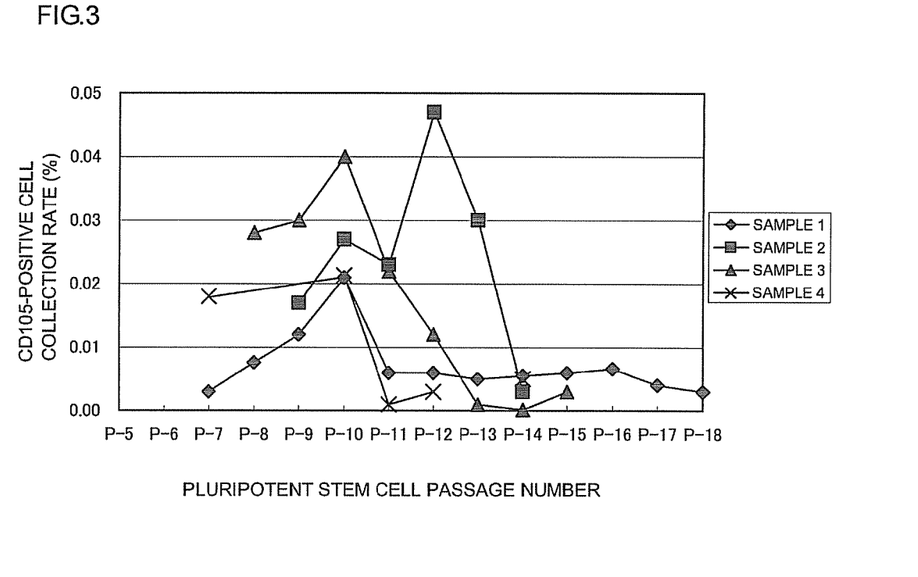
FIG. 3 is a graph showing the yield of CD105-positive cells versus the passage number of pluripotent stem cells.

A correlation was investigated between the yield of the CD105-positive cells separated and collected using the MACS® method as described above and the passage number of pluripotent stem cells. Namely, after thawing cryopreserved undifferentiated pluripotent stem cells, Sample 1 sub-cultured 7 to 18 times, Sample 2 sub-cultured 9 to 14 times, Sample 3 sub-cultured 8 to 15 times and Sample 4 sub-cultured 7 or 10 to 12 or 14 times were induced to differentiate into adipocytes as previously described, followed by separating those cells that were CD105 positive during the course of culturing and determining the yield. FIG. 3 is a graph showing the yield of CD105-positive cells versus the passage number of each sample. Passage number is plotted on the horizontal axis, while yield of the separated CD105-positive cells is plotted on the vertical axis.

As is clear from FIG. 3, Samples 1, 3 and 4 demonstrated the highest yields of separated CD105-positive cells in the case of pluripotent stem cells sub-cultured 10 times, while Sample 2 demonstrated the highest yield of separated CD105-positive cells in the case of using pluripotent stem cells sub-cultured 12 times. In addition, CD105-positive cells were confirmed to be able to be separated at high yield for all of the samples in the case of using pluripotent stem cells sub-cultured 8 to 12 times.

[FACS Analysis of CD105-Positive Cells]

Next, the purity of the CD105-positive cells separated by MACS® was analyzed by fluorescence activated cell sorting (FACS®) using fluorescent-labeled anti-mouse CD105 monoclonal antibody to evaluate separation performance.

Namely, pluripotent stem cells that had been sub-cultured 10 times and demonstrated the highest yield of CD105-positive cells were induced to differentiate into adipocytes, and the cells were adhered to a culture dish followed by dissociating cells cultured in adipogenic culture medium. Cells were then obtained by removing the supernatant from a cell suspension in which the cells were suspended in the MACS buffer.

Anti-mouse CD105 monoclonal antibody (Clone: 209701, FAB1320P, R&D) labeled with a fluorescent dye (Phycoerythrin: PE) and diluted 10-fold with PBS was added to the cells as primary antibody followed by carrying out an antigen-antibody reaction for 10 minutes at 4° C. Next, the MACS® buffer was added to the test cells and the cells were washed by centrifuging for 10 minutes at 1000 rpm to remove excess primary antibody. Subsequently, anti-PE microbeads (130-048-801, Miltenyl Biotech) diluted 8-fold with PBS were added as secondary antibody to the washed test cells followed by carrying out an antigen-antibody reaction for 15 minutes at 4° C. The test cells were washed in the same manner as after the reaction with the primary antibody to remove excess secondary antibody.

The cell suspension containing cells labeled with the microbeads obtained in the manner described above was passed through a mini-MACS® separation column (Miltenyl Biotech) according to the manual provided by the manufacturer. As a result, the CD105-positive cells were selectively separated. Furthermore, the CD105-positive cells were separated by carrying out separation by the mini-MACS separation column twice in succession to enhance cell purity.

Figure 4:
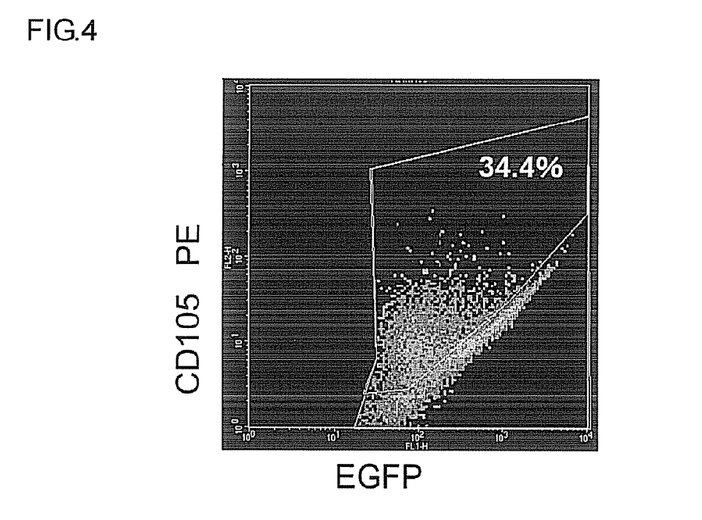
FIG. 4 shows the results of FACS® analysis of a cell group that has not been separated by MACS®.
Figure 5:
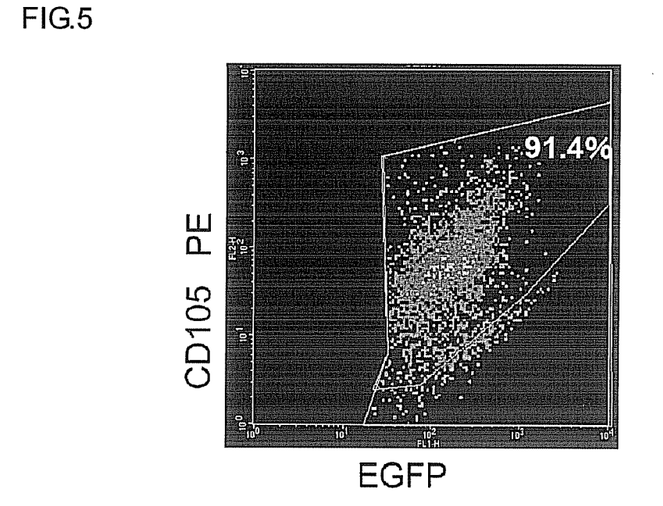
FIG. 5 shows the results of FACS® analysis of a cell group (CD105-positive cell group) that has been separated by MACS®.

A cell group separated by MACS® using the fluorescent-labeled anti-mouse CD105 monoclonal antibody (CD105-positive cell group) and a cell group not separated by MACS® were analyzed for PE-positive cells using an FACS® Calibur flow cytometer (BD). FIG. 4 shows the cell group that was not separated by MACS®, while FIG. 5 shows the CD105-positive cell group separated by MACS®. Furthermore, image corrections required for quantitative analysis were made at the wavelength of Enhanced GFP (EGFP).

As a result of FACS analysis, the cell group not separated by MACS was confirmed to contain 34.4% PE-positive CD105-positive cells as shown in FIG. 4. In addition, the cell group that was separated by MACS was confirmed to contain 91.4% PE-positive CD105-positive cells as shown in FIG. 5. On the basis of these results, CD105-positive cells were demonstrated to be able to be separated and collected at high purity by using MACS®.

Figure 6:
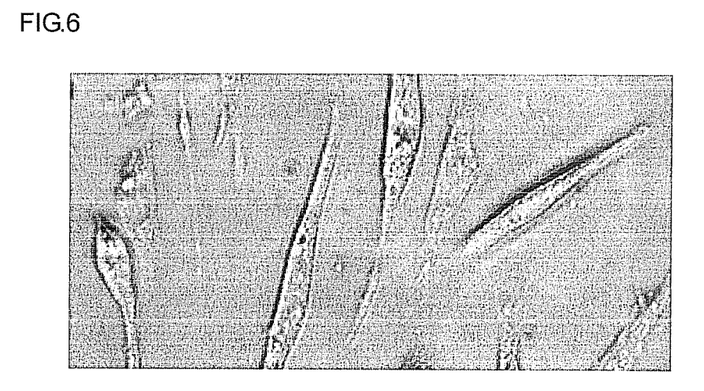
FIG. 6 is a micrograph of a cell group that has been separated by MACS® as observed with a position scanning microscope.

Moreover, the cell group separated by MACS® as described above was observed with a position scanning microscope. FIG. 6 is a micrograph of CD105-positive cells taken with a position scanning microscope.

As shown in FIG. 6, the CD105-positive cells were confirmed to have a fusiform shape that resembled extremely closely the cell morphology of ADSCs separated from adipocytes.

[Confirmation of Cells Expressed by Inducing Differentiation]

Whether or not the CD105-positive cells separated by MACS as described above are induced to differentiate into adipocytes, osteocytes, chondrocytes or myoblasts differentiated into a target form was confirmed by culturing the CD105-positive cells under respective conditions that enable them to be induced to differentiate into adipocytes, osteocytes, chondrocytes or myoblasts.

Namely, the CD105-positive cells separated by MACS as described above were disseminated into a culture dish coated with gelatin at a low density ($1 \times 10^3$ to $2.5 \times 10^3$ cells/cm$^2$), followed by culturing for 2 to 3 weeks in ES-DMEM culture broth capable of inducing differentiation into each cell. The ES-DMEM culture broth was replaced every 2 days and was composed of the respective compositions indicated below.

Furthermore, whether or not the cell group not separated by MACS (to be referred to as "CD105-negative cells") is induced to differentiate into adipocytes, osteocytes, chondrocytes or myoblasts was confirmed by culturing for 2 to 3 weeks under respective conditions that enable induction of differentiation into adipocytes, osteocytes, chondrocytes or myoblasts.

Although various known culture broths for inducing differentiation into adipocytes can be employed for inducing differentiation into adipocytes, ES-DMEM culture broth was used here in which 0.005% insulin (I-1882, Sigma), 0.007% 3,3,5-triiodo-L-thyronine (Triiodothyronine (T3), T5516, Sigma), 1 µM dexamethasone (D4902-25MG, Sigma) and 500 µM 3-isobutyl-1-methyl-xanthin (IBMX: 15879-100MG, Sigma) were added to ES-DMEM.

Although various known culture broths for inducing differentiation into osteocytes can be employed for inducing differentiation into osteocytes, ES-DMEM culture broth was used here in which 0.1 µM dexamethasone (D4902-25MG, Sigma), 10 mM β-glycerol phosphate (37177-30, Kanto Chemical) and 200 µM ascorbic acid (A4544-25G, Sigma) were added to ES-DMEM.

Although various known culture broths for inducing differentiation into chondrocytes can be employed for inducing differentiation into chondrocytes, a culture broth was used here in which 10 ng/mL of TGFβ3 (243-B3, Sigma), 100 nM PTH (parathyroid hormone: 12583-68-5, Sigma) and 1% FBS were added to serum-free ES-DMEM.

Although various known culture broths for inducing differentiation into myoblasts can be employed for inducing differentiation into myoblasts, a culture broth was used here in which 5% serum replacement (KSR:Knockout™ Serum Replacement: 10828-028, INVITROGEN®) was added to serum-free ES-DMEM.

The cells resulting from inducing differentiation were observed and their cell type was identified. Identification of cell type was carried out according to the methods described below.

Those cells that were induced to differentiate into adipocytes were identified by staining with Oil Red O. A solution of 0.3% Oil Red O (115K0683, Sigma) and 1-propanol (24-6070-5, Sigma) was used as a cell preserver, and this cell preserver was diluted at a ratio of 6:4 with distilled water and filtered for use as Oil Red O staining solution. In addition, hematoxylin stain was used to simultaneously stain the cell nuclei.

First, the cultured cells were washed twice with PBS and fixed by immersing for 30 minutes in 4% paraformaldehyde (24-0630-5, SIGMA®) dissolved in PBS. Next, the fixed test cells were washed for 30 minutes with PBS and then allowed to react for 1 minute in 60% 1-propanol. The above-mentioned Oil Red O staining solution was added followed by allowing to react for 15 minutes at 37° C. Subsequently, the cells were allowed to react for 2 minutes in 60% 1-propanol followed by washing for 2 minutes with distilled water.

Subsequently, the cell nuclei were stained for 5 minutes with hematoxylin and then washed for 2 minutes with distilled water. Finally, the cells were sealed in 80% glycerol (12-1120-5, SIGMA®) diluted with PBS.

Figure 7:
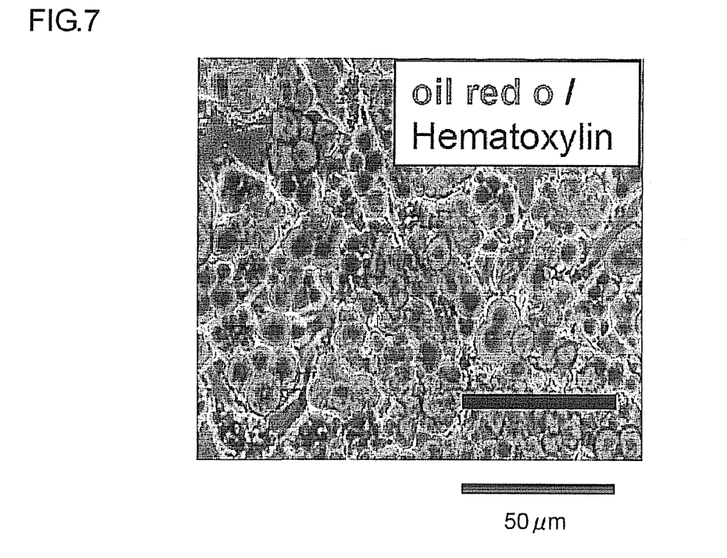
FIG. 7 is a micrograph depicting CD105-positive cells that have been induced to differentiate into adipocytes stained with Oil Red O.
Figure 8:
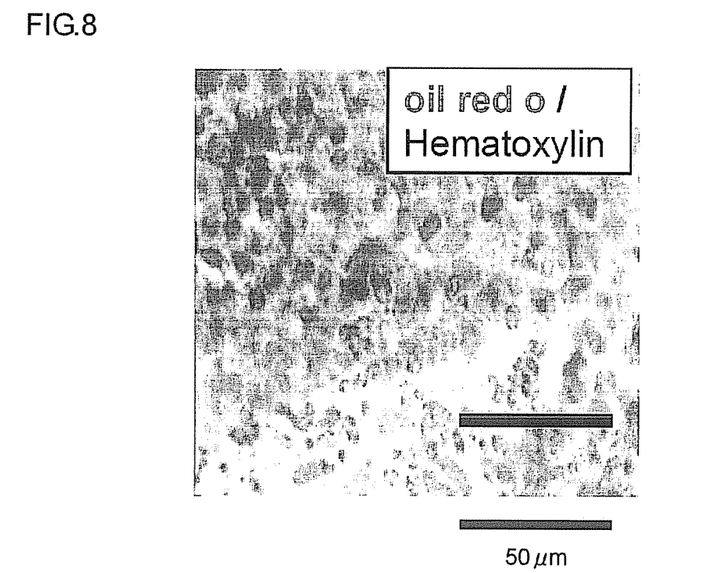
FIG. 8 is a micrograph depicting CD105-positive cells that have been induced to differentiate into adipocytes stained with Oil Red O.

Micrographs of the cells stained with Oil Red O as described above are shown in FIGS. 7 and 8. FIG. 7 depicts CD105-positive cells, while FIG. 8 depicts CD105-negative cells.

Those cells that were expressed and induced to differentiate into osteocytes were confirmed using Alizarin red stain. First, 28% aqueous ammonia (MKD1711, Yoneyama Yakuhin) was slowly added to a 1% aqueous solution of Alizarin red S (A5533-25G, SIGMA®), and used as an Alizarin red staining solution after adjusting the pH to 6.36 to 6.40. The cells were washed twice with PBS and fixed for 30 minutes with 4% paraformaldehyde (24-0630-5, SIGMA®). The fixed cells were further washed several times with distilled water followed by adding the Alizarin red staining solution and allowing to react for 5 minutes. Finally, the cells were washed several times with distilled water and sealed in glycerol.

Figure 9:
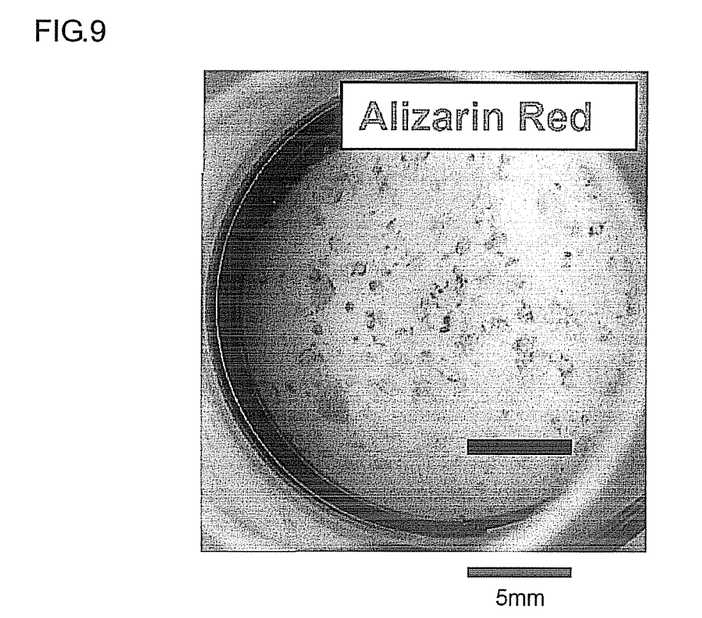
FIG. 9 is a micrograph depicting CD105-positive cells that have been induced to differentiate into osteocytes stained with Alizarin red.
Figure 10:
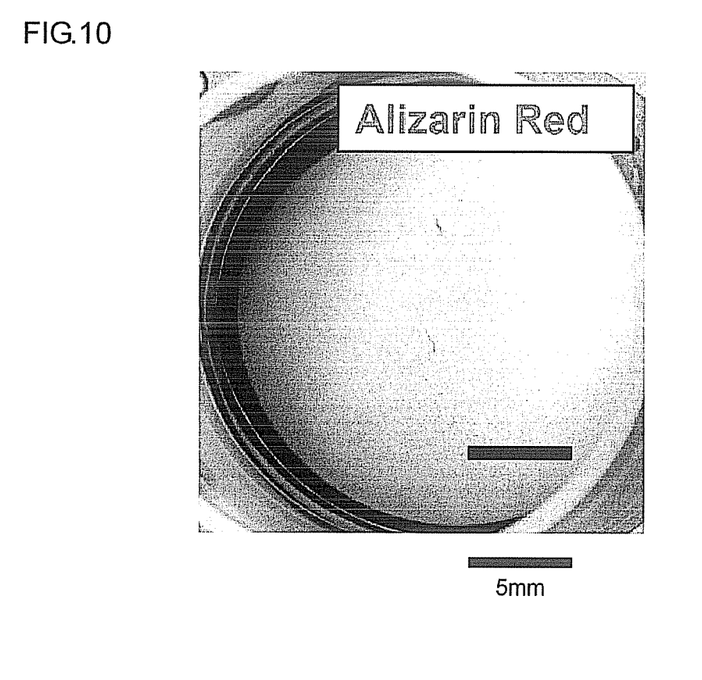
FIG. 10 is a micrograph depicting CD105-positive cells that have been induced to differentiate into osteocytes stained with Alizarin red.

Micrographs of the cells stained with Alizarin red as described above are shown in FIGS. 9 and 10. FIG. 9 depicts CD105-positive cells, while FIG. 10 depicts CD105-negative cells.

In addition, those cells that were expressed and induced to differentiate into chondrocytes were confirmed using Alcian blue stain. First, the cells were washed twice with PBS followed by fixing for 15 minutes in a fixing solution containing 4% paraformaldehyde (24-0630-5, SIGMA®) in PBS. Subsequently, the cells were washed for 15 minutes with PBS and then further washed for 5 minutes with 3% aqueous acetic acid solution. After washing, 1 g of Alcian blue 8GX was dissolved in 100 ml of 3% aqueous acetic acid solution to prepare an Alcian blue staining solution, and the cells were then stained for 30 minutes by adding this staining solution thereto. The cells were then washed for 5 minutes with 3% aqueous acetic acid solution and then further washed for 5 minutes with distilled water. Finally, the cells were sealed in 80% glycerol (12-1120-5, SIGMA®) diluted with PBS.

Figure 11:
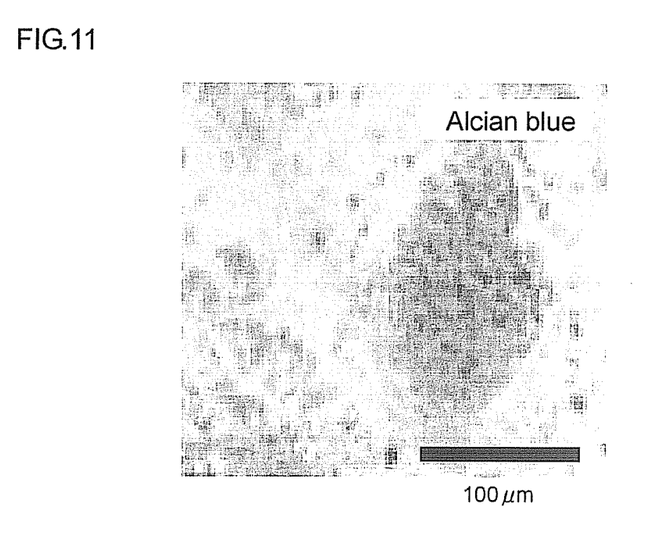
FIG. 11 is a micrograph depicting CD105-positive cells that have been induced to differentiate into chondrocytes stained with Alcian blue.
Figure 12:
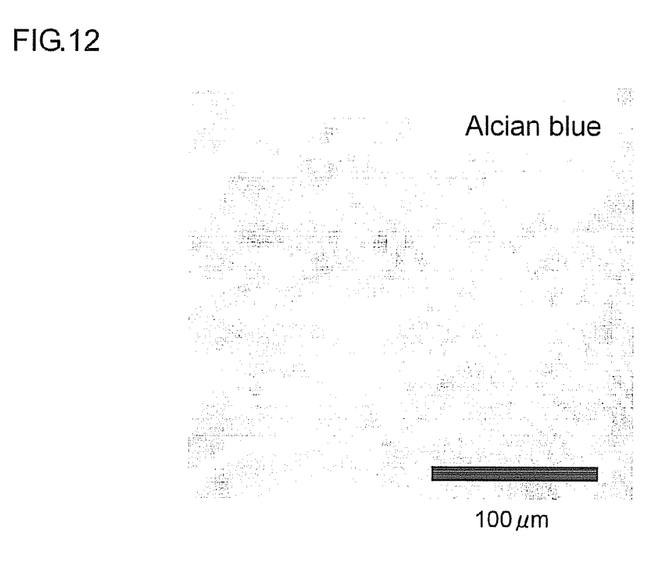
FIG. 12 is a micrograph depicting CD105-positive cells that have been induced to differentiate into chondrocytes stained with Alcian blue.

Micrographs of the cells stained with Alcian blue as described above are shown in FIGS. 11 and 12. FIG. 11 depicts CD105-positive cells, while FIG. 12 depicts CD105-negative cells.

Moreover, those cells that were expressed and induced to differentiate into myoblasts were respectively confirmed by immunofluorescent staining using anti-M-cadherin antibody and immunofluorescent staining using anti-myosin heavy chain (MHC) antibody. After washing twice with PBS, the cells were fixed for 15 minutes in a fixing solution containing 4% paraformaldehyde (24-0630-5, Sigma) in PBS. Subsequently, the cells were washed for 15 minutes with PBS followed by the addition of a blocking solution in which normal goat antiserum (G9023, Sigma) was diluted to 10% with 0.1% Triton PBS to inhibit non-specific reactions for 30 minutes at 37° C. Next, primary antibodies consisting of anti-myosin heavy chain antibody (MHC: clone A4: 1025, Upstate) and anti-M-cadherin antibody (Clone: 12G4, Nanotools) diluted 200-fold and 100-fold respectively with 0.1% Triton PBS were added, and antigen-antibody reactions were carried out for 1 hour at 37° C. Following the reactions, the cells were washed for 15 minutes with PBS. Moreover, Alexa 594-labeled mouse IgG antibody (A11001, Molecular Probes) serving as secondary antibody diluted 200-fold with 0.1% Triton PBS was added, and an antigen-antibody reaction was carried out for 1 hour at 37° C. Subsequently, the cells were washed for 15 minutes with PBS at room temperature and sealed in a sealing agent that prevents fluorescent bleaching (PermaFluor™: 43499, Thermo). Micrographs of CD105-positive cells immunofluorescent-stained using M-cadherin and MCH as described above are respectively shown in FIGS. 13 and 14.

Results of identifying each of the cells expressed under conditions enabling them to be induced to differentiate into the above-mentioned target adipocytes, osteocytes, chondrocytes and myoblasts are described below.

First, in the case of inducing differentiation into adipocytes, as shown in FIGS. 7 and 8, the CD105-positive cells of FIG. 7 were confirmed to be adipocytes by Oil Red O staining. On the other hand, the CD105-negative cells of FIG. 8 were confirmed to not have expressed adipocytes despite having been induced to differentiate into adipocytes.

In addition, in the case of inducing differentiation into osteocytes, as shown in FIGS. 9 and 10, the CD105-positive cells of FIG. 9 were confirmed to be osteocytes by Alizarin red staining. On the other hand, the CD105-negative cells of FIG. 10 were confirmed to not have expressed osteocytes despite having been induced to differentiate into osteocytes.

In addition, in the case of inducing differentiation into chondrocytes, as shown in FIGS. 11 and 12, the CD105-positive cells of FIG. 11 were confirmed to be chondrocytes by Alcian blue staining. On the other hand, the CD105-negative cells of FIG. 12 were confirmed to not have expressed chondrocytes despite having been induced to differentiate into chondrocytes.

Figure 13:
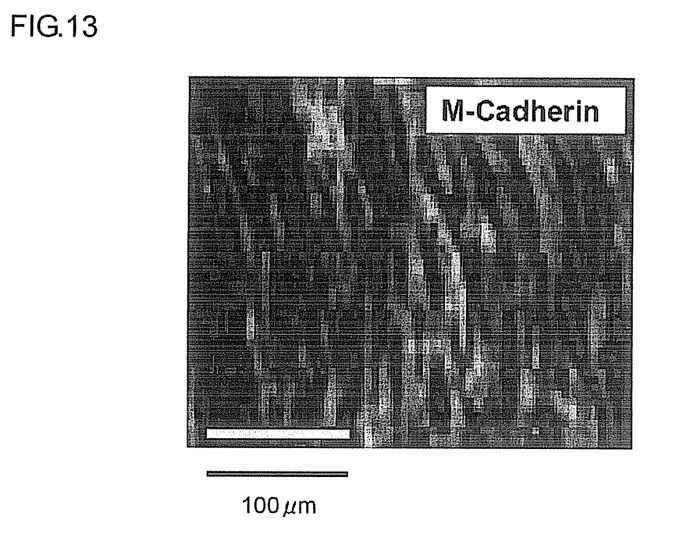
FIG. 13 is a micrograph depicting CD105-positive cells that have been induced to differentiate into myoblasts immunofluorescent-stained with M-cadherin.
Figure 14:
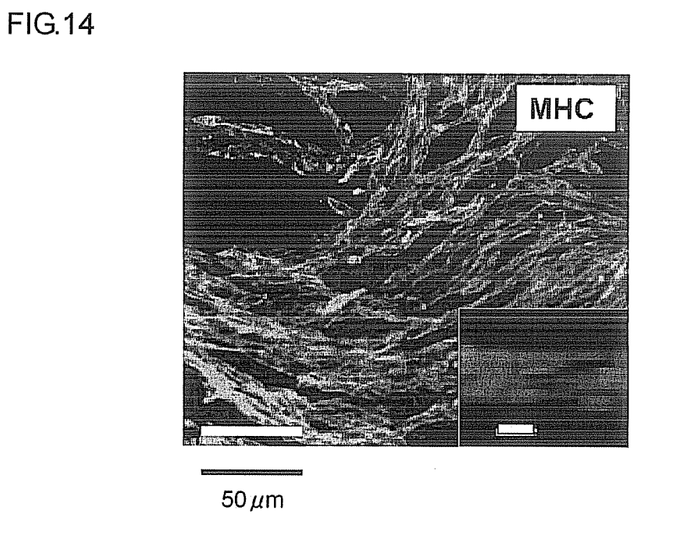
FIG. 14 is a micrograph depicting CD105-positive cells that have been induced to differentiate into myoblasts immunofluorescent-stained with MHC.

Moreover, in the case of inducing differentiation into myoblasts, as shown in FIGS. 13 and 14, the CD105-positive cells were confirmed to be myoblasts for both the M-cadherin immunofluorescent staining of FIG. 13 and the myosin heavy chain (MHC) immunofluorescent staining of FIG. 14. In addition, although not shown in the drawings, CD105-negative cells were confirmed to not have expressed myoblasts despite having been induced to differentiate into myoblasts.

[RT-PCR Analysis]

Next, an analysis was conducted using RT-PCR as to whether or not CD105-positive cells separated by MACS® as described above are inducted to differentiate into target cells by culturing under respective conditions enabling the CD105-positive cells to be induced to differentiate into adipocytes, osteocytes, chondrocytes or myoblasts.

Although conventionally known, common methods can be employed for RT-PCR analysis, RT-PCR analysis was carried out here according to the method described below.

Namely, cells that had been induced to differentiate that were adhered to a culture dish were separated using a cell scraper and crushed with an ultrasonic homogenizer (Handy Sonic, Tomy Seiko). Only mRNA was collected using an RNA extraction kit (RNeasy, Quiagen) and the amount of mRNA was determined with an absorption spectrophotometer (Nanodrop). cDNA to serve as template was then synthesized from the collected RNA with Superscript Reverse Transcriptase II (Invitrogen) serving as reverse transcriptase using Oligo (dT) Primer (18418-012, Invitrogen). BLEND TAG™ (TOYOBO®) as Taq DNA polymerase, the buffer provided therewith (BTQ-101, TOYOBO®), and the following primers specific for the gene of each cell were respectively used in PCR. PPARγ and LPL were used as adipocyte primers, and Runx2 and Osterix were used as osteocyte primers. In addition, Collagen 2al and Agglycan were used as chondrocyte primers, and M-cadherin, MHC, MyoD and Myf5 were used as myoblast primers. In addition, the cycle conditions of the PCR reaction were such that each cycle was composed of 60 seconds at 95° C., 30 seconds at 60° C. and 30 seconds at 70° C., and the reaction was carried out for a total of 36 cycles. Following completion of 36 cycles, the PCR product was applied to 2% agarose gel (800171, Nippon Gene) and electrophoresed with Mulpid-2plus (100 V, 45 minutes: Advance). The electrophoresed agarose gel was stained using CYBR Safe DNA Gel Stain (54022A, Invitrogen), and each specific band was detected with FAS-III (TOYOBO®).

As a result of RT-PCR analysis, PPARγ and LPL mRNA bands (not shown) specifically expressed by adipocytes were confirmed for those cells induced to differentiate into adipocytes. In addition, Runx2 and Osterix mRNA bands (not shown) specifically expressed in osteocytes were confirmed for those cells induced to differentiate into osteocytes. Collagen 2al and Agglycan mRNA bands (not shown) specifically expressed in chondrocytes were confirmed for those cells induced to differentiate into chondrocytes. Moreover, M-cadherin, MHC, MyoD and Myf5 mRNA bands (not shown) specifically expressed in myoblasts were confirmed for those cells induced to differentiate into myoblasts.

On the basis of the above results, CD105-positive cells separated by MACS were demonstrated to be mesenchymal stem cells provided with the ability to expressed at a high rate cells differentiated into a target form (adipocytes, osteocytes, chondrocytes or myoblasts). In addition, adipocytes, osteocytes, chondrocytes or myoblasts derived from pluripotent stem cells were confirmed to be able to be provided by the production method and cell culture disclosed herein.

[Confirmation of Differentiation Ability Using Pluripotent Stem Cells Having Different Passage Numbers]

Moreover, CD105-positive cells were separated by inducing differentiation into adipocytes using pluripotent stem cells having different passage numbers. Each of the separated CD105-positive cells was induced to differentiate into adipocytes or myoblasts followed by observing the cells.

<Sample A>

Pluripotent stem cells were sub-cultured 10 times using undifferentiated, cryopreserved mouse-derived ES cells in the same manner as in the previously described embodiment for the pluripotent stem cells. After designating these cells as Sample A and sub-culturing the ES cells 10 times, the ES cells were induced to differentiate into adipocytes in vitro using the method previously described, and CD105-positive cells were separated using MACS. The separated CD105-positive cells were then cultured for 20 days under conditions enabling induction of differentiation into myoblasts, and the cells resulting from induction of differentiation were observed.

<Sample B>

For Sample B, cryopreserved, mouse-derived ES cells were then used as pluripotent stem cells and sub-cultured in the same manner as Sample A. However, the passage number was changed to 5 times.

With the exception of the above, induction of differentiation into adipocytes was carried out using the sub-cultured pluripotent stem cells according to the same procedure as Sample A, and CD105-positive cells were separated using MACS.

Moreover, the separated CD105-positive cells were further cultured for 20 days under conditions enabling induction of differentiation into myoblasts in vitro in the same manner as Sample A, and the cells resulting from induction of differentiation were observed.

<Sample C>

For Sample C, cryopreserved, mouse-derived ES cells were then used as pluripotent stem cells and sub-cultured in the same manner as Sample A. However, the passage number was changed to 17 times.

With the exception of the above, induction of differentiation into adipocytes was carried out using the sub-cultured pluripotent stem cells according to the same procedure as Sample A, and CD105-positive cells were separated using MACS.

Moreover, the separated CD105-positive cells were further cultured for 20 days under conditions enabling induction of differentiation into myoblasts in vitro in the same manner as Sample A, and the cells that differentiated during the course of culturing were observed.

As a result of microscopic observations, cells that had been induced to differentiate into myoblasts in Sample A were confirmed to be fusiform myoblasts (not shown). Thus, CD105-positive cells contained in the cell culture relating to Sample A were demonstrated to mesenchymal stem cells provided with the ability to be able to differentiate into myoblasts with high efficiency. In addition, myoblasts derived from pluripotent stem cells were confirmed to be able to be provided by the production method and cell culture disclosed herein.

On the other hand, although cells that had been induced to differentiate into myoblasts were microscopically observed in Samples B and C, the presence of fusiform cells was not confirmed. Therefore, when the pluripotent stem cells of Samples B and C were induced to differentiate into adipocytes and then stained with Oil Red O stain, the cells resulting following induction of differentiation of Samples B and C (not shown) were stained red, thereby confirming them to be adipocytes. Thus, the CD105-positive cells relating to Samples B and C that had different passage numbers than that of Sample A were demonstrated to be mesenchymal stem cells able to differentiate into adipocytes at a high probability. On the basis thereof, CD105-positive cells separated after inducing pluripotent stem cells having a passage number of 10 times to differentiate into adipocytes were confirmed to be induced to differentiate into myoblasts at high efficiency. In addition, when pluripotent stem cells having a passage number of 5 or 17 times are induced to differentiate into adipocytes, only a small number of CD105-positive cells were able to be collected. However, although myoblasts were unable to be confirmed in microscopic observations of those cells that were induced to differentiate into myoblasts, expression of adipocytes was confirmed when induced to differentiate into adipocytes.

INDUSTRIAL APPLICABILITY

As is clear from the above-mentioned embodiment, according to the present invention, a method can be provided for producing efficiently and in large quantities mesenchymal stem cells able to differentiate into myoblasts or other target cells during the course of inducing pluripotent stem cells to differentiate into adipocytes. Thus, according to the present embodiment, myoblasts, which were conventionally a cell type for which it was difficult to induce differentiation from mesenchymal stem cells, were able to be produced in large quantities from pluripotent stem cells.

The invention claimed is:

1. A method for producing a myoblast by culturing mouse-derived pluripotent stem cells, the method comprising:
   i) preparing the mouse-derived pluripotent stem cells that have been cryopreserved;
   ii) sub-culturing the prepared mouse-derived pluripotent stem cells 8 to 12 times in an undifferentiated state, wherein the mouse-derived pluripotent stem cells are sub-cultured in a medium containing leukemia inhibitory factor (LIF);
   iii) culturing the subcultured mouse-derived pluripotent stem cell under conditions that enable induction of differentiation into an adipocyte in vitro, wherein the conditions include suspension-culturing in a medium containing retinoic acid for 2 to 3 days, followed by culturing in a medium containing insulin and triiodothyronine (T3), and wherein the time period of the iii) culturing is 7 to 21 days from the start of the culturing following the ii) sub-culturing;
   iv) separating and collecting a CD105-positive mesenchymal stem cell after the culturing in the medium containing insulin and T3; and
   v) further culturing the separated and collected CD105-positive cell under conditions that enable induction of differentiation into a myoblast in vitro, wherein the collected CD105-positive cells are cultured in ES cell culture medium containing serum or serum replacement.

2. The method according to claim 1, wherein the iii) culturing the subcultured mouse-derived pluripotent stem cell under conditions that enable induction of differentiation into an adipocyte is carried out for 7 to 14 days.

3. The method according to claim 1, wherein the ii) sub-culturing the prepared mouse-derived pluripotent stem cell is carried out 9 to 11 times.

4. The method according to claim 1, wherein the mouse-derived pluripotent stem cells are mouse ES cells are mouse iPS cells.

* * * * *